United States Patent [19]

Kingsman et al.

[11] Patent Number: 5,008,373

[45] Date of Patent: * Apr. 16, 1991

[54] FUSION PROTEINS AND PARTICLES

[75] Inventors: Alan J. Kingsman; Susan M. Kingsman, both of Islip; Sally E. Adams, Kidlington; Elizabeth J. C. Mellor, Oxford; Michael H. Malim, Upleadon, all of United Kingdom

[73] Assignee: Oxford Gene Systems Limited, Oxford, England

[*] Notice: The portion of the term of this patent subsequent to Apr. 17, 2007 has been disclaimed.

[21] Appl. No.: 112,082

[22] Filed: Oct. 26, 1987

Related U.S. Application Data

[63] Continuation-in-part of Ser. No. 36,807, Apr. 10, 1987.

[30] Foreign Application Priority Data

Nov. 1, 1986 [GB] United Kingdom ............... 8626148
Sep. 4, 1987 [GB] United Kingdom ............... 8708531

[51] Int. Cl.[5] .................... C07K 3/00; C02K 13/00; C02K 15/00; C12N 15/11

[52] U.S. Cl. .................. 530/350; 435/69.7; 435/91; 435/170; 435/171; 435/172.3; 435/240.2; 435/252.3; 435/254; 435/257; 435/235; 435/258; 435/320.1; 536/27; 530/351; 530/412; 935/10; 935/12; 935/22; 935/59; 935/66

[58] Field of Search ............... 435/69.7, 91, 170, 171, 435/172.3, 240.2, 252.3, 254, 257, 258, 320, 235; 536/27; 530/300, 324, 325, 326, 344, 350, 351, 412; 935/10, 12, 22, 59, 66

[56] References Cited

U.S. PATENT DOCUMENTS 4,722,840   2/1988   Valenzuela et al. ................. 424/88
4,925,784  12/1990   Crowl et al. ............................ 435/5

OTHER PUBLICATIONS

Haynes et al., 1986, *Bio/Technology*, 4:637.
Mellor et al., 1985, *Nature*, 317:243.

*Primary Examiner*—Richard A. Schwartz
*Assistant Examiner*—Richard C. Peet
*Attorney, Agent, or Firm*—Allegretti & Witcoff, Ltd.

[57] ABSTRACT

Fusion proteins comprise a first amino acid sequence and a second amino acid sequence. The first amino acid sequence is derived from a retrotransposon or an RNA retrovirus and confers on the fusion protein the ability of assemble into particles; an example is the product of the TYA gene of the yeast retrotransposon Ty. The second amino acid sequence is biologically active; for example, it may be antigenic. So particles formed of the fusion proteins may be useful in vaccines or in diagnostic or purification applications

5 Claims, 17 Drawing Sheets

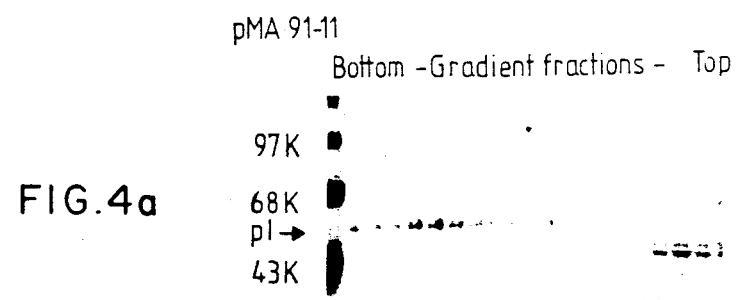
FIG.4a
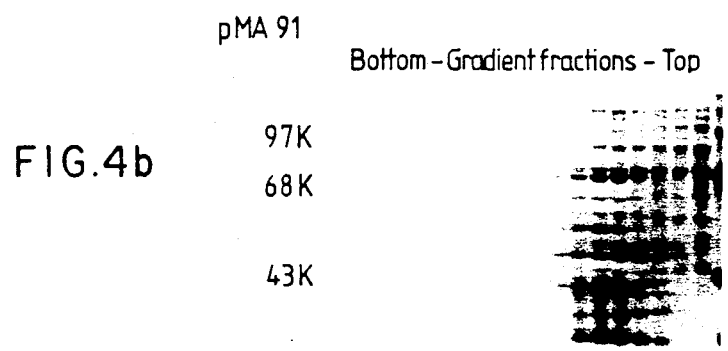
FIG.4b
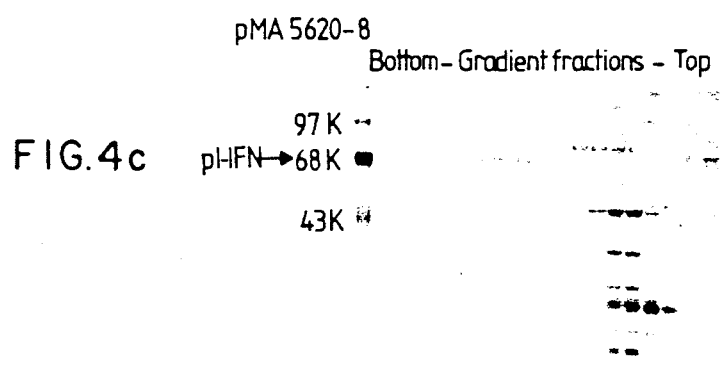
FIG.4c
FIG.1

Ty-VLP ANTIBODY

IFN ANTIBODY

FIG. 7

Ty : IFN
FUSION PROTEIN 1  2  3

97K

68K

25K

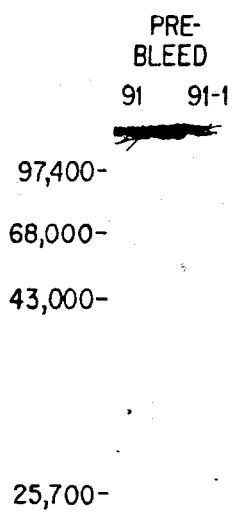
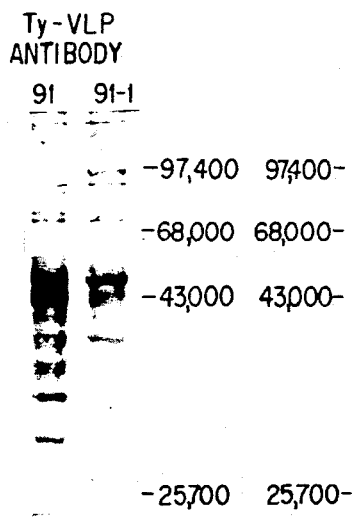
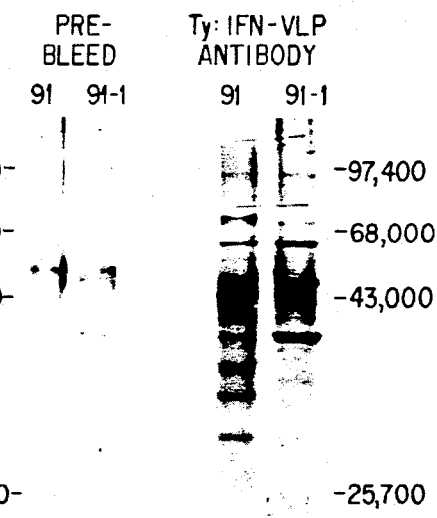
FIG. 8a  FIG. 8b  FIG. 8c  FIG. 8d

FIG. 9

```
    SpeI
A   CTA GTG AAA ACA ATC ACA AAT GAT CAG ATT GAA
    25              30                      35
    GTG ACT AAT GCT ACT GAG CTG GTT CAG AGT TCC
                    40                  45
    TCA ACG GGG AAA ATA TGC AAC AAT CCT CAT CGA
                50              55
    ATC CTT GAT GGA ATA GAC TGC ACA CTG ATA GAT
            60                  65
    GCT CTA TTG GGG GAC CCT CAT TGT GAT GGC TTT
        70              75
    CAA AAT GAG ACA TGG GAC CTT TTC GTT GAA CGC
    80                  85                  90
    AGC AAA GCT TTC AGC AAC TGT TAC CCT TAT GAT
                    95                  100
                                            SpeI
    GTG CCA GAT TAT GCC TCC CTT AGG TTA CTA GT
                105                 110
```

T 5620

Ty protein → fraction number  1 2 3 4 5 6 7 8 9 10 11 12 13 14 15 16 17 18 19 bottom          top

T 5620-HA23

Ty:HA → fusion protein fraction number  1 2 3 4 5 6 7 8 9 10 11 12 13 14 15 16 17 18 19 bottom          top

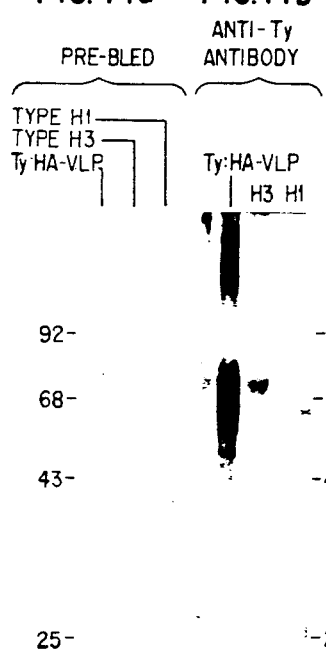
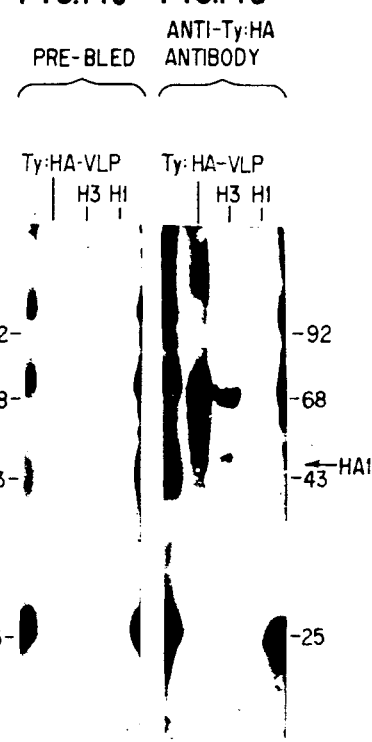
FIG. 14a  FIG. 14b  FIG. 14c  FIG. 14d  FIG. 14e

FIG. 16

```
ATGGAATCCCAACAATTATCTCAACATTCACCCATTTCTCATGGTAGC
 M  E  S  Q  Q  L  S  Q  H  S  P  I  S  H  G  S

GCCTGTGCTTCGGTTACTTCTAAGGAAGTCCACACAAATCAAGATCCG
 A  C  A  S  V  T  S  K  E  V  H  T  N  Q  D  P

TTAGACGTTTCAGCTTCCAAAACAGAAGAATGTGAGAAGGCTTCCACT
 L  D  V  S  A  S  K  T  E  E  C  E  K  A  S  T

AAGGCTAACTCTCAACAGACAACAACACCTCCTTCATCAGCTGTTCCA
 K  A  N  S  Q  Q  T  T  T  P  A  S  S  A  V  P

GAGAACCCCCATCATGCCTCTCCTCAAACTGCTCAGTCACATTCACCA
 E  N  P  H  H  A  S  P  Q  T  A  Q  S  H  S  P

CAGAATGGGCGGTACCCACAGCAGTGCATGATGACCCAAAACCAAGCC
 Q  N  G  P  Y  P  Q  Q  C  M  M  T  Q  N  Q  A

AATCCATCTGGTTGGTCATTTTACGGACACCCATCTATGATTCCGTAT
 N  P  S  G  W  S  F  Y  G  H  P  S  M  I  P  Y

ACACCTTATCAAATGTCGCCTATGTACTTTCCACCTGGGCCACAATCA
 T  P  Y  Q  M  S  P  M  Y  F  P  P  G  P  Q  S

CAGTTTCCGCAGTATCCATCATCAGTTGGAACGCCTCTGAGGACTCCA
 Q  F  P  Q  Y  P  S  S  V  G  T  P  L  R  T  P

TCACCTGAGTCAGGTAATACATTACTGATTCATCCTCAGCGGACTCT
 S  P  E  S  G  N  T  P  T  D  S  S  A  D  S

GATATGACATCCACTAAAAAATATGTCAGACCACCACCAATGTTAACC
 D  M  T  S  T  K  K  Y  V  R  P  P  P  M  L  T

TCACCTAATGACTTTCCAAATTGGGTTAAAACATACATCAAATTTTTA
 S  P  N  D  F  P  N  W  V  K  T  Y  I  K  F  L

CAAAACTCGAATCTCGGTGGTATTATTCCGACAGTAAACGGAAAACCC
 Q  N  S  N  L  G  G  I  I  P  T  V  N  G  K  P

GTACGTCAGATCATCGATGATGAACTCACCTTCTTGTATAACACTTTT
 V  P  Q  I  T  D  D  E  L  T  F  L  Y  N  T  F

CAAATATTTGCTCCCTCTCAATTCCTACCTACCTGGGTCAAAGACATC
 Q  I  F  A  P  S  Q  F  L  P  T  W  V  E  D  I

CTATCCGTTGATTATACGGATATCATGAAAATTCTTTCCAAAAGTATT
 L  S  V  D  Y  T  D  I  M  K  I  L  S  K  S  I
```

FIG. 16 cont.

```
GAAAAAAATGCAATCTGATACCCAAGAGGCAAACGACATTGTGACCCTG
 E  K  N  Q  S  D  T  Q  E  A  N  D  I  V  T  L

GCAAATTTGCAATATAATGGCAGTACACCTGCAGATGCATTTGAAACA
 A  N  L  Q  Y  N  G  S  T  P  A  D  A  F  E  T

AAAGTCACAAACATTATCGACAGACTGAACAATAATGGCATTCATATC
 K  V  T  N  I  I  D  R  L  N  N  N  G  I  H  I

AATAACAAGGTCGCATGCCAATTAATTATGAGAGGTCTATCTGGCGAA
 N  N  K  V  A  C  Q  L  I  M  R  G  L  S  G  E

TATAAATTTTTACGCTACACACGTCATCGACATCTAAATATGACAGTC
 Y  K  F  L  R  Y  T  R  H  R  N  L  N  H  T  V

GCTGAACTGTTCTTAGATATCCATGCTATTTATGAAGAACAACAGGGA
 A  E  L  F  L  D  I  H  A  I  Y  E  E  Q  Q  G

TCGAGAAACAGTAAACCTAATTACAGGAGAAATCCGAGTGATGAGAAG
 S  R  N  S  K  P  N  Y  R  R  N  P  S  D  E  K

AATGATTCTCGCAGCTATACGAATACAACCAAACCCAAAGccggatc
 N  D  S  R  S
```

FUSION PROTEINS AND PARTICLES

This is a continuation-in-part of Ser. No. 07/036,007 filed Apr. 10, 1987, now pending.

TECHNICAL FIELD

The present invention relates to an antigen presentation and purification system. In particular embodiments it relates to particles encoded by the yeast tetrotransposon Ty, a vector containing the gene for particle formation, a vector for the high level expression of fusions of the particle protein and any antigen and a method for the production and purification of these fusion proteins in yeast.

BACKGROUND ART

One of the most important applications of the new recombinant DNA technology is in the production of safe vaccines against infectious diseases and the synthesis of defined proteins against which antisera can be raised for experimental, industrial and diagnostic purposes. Theoretically, these goals can be achieved by the synthesis of appropriate antigens in microorganisms such as the yeast *Saccharomyces cerevisiae*. The antigen would be expressed from an appropriate expression vector such as described in European Patent Application EPA2-0073635.

Correct presentation of the antigen to an animal or human immune system is a key requirement for an effective sub-unit vaccine or immunogen. Presentation has been a major problem with potential vaccines and immunogens made by recombinant DNA as well as for those based on chemically synthesized epitopes. An ideal immunogen is a polymer of multiple antigenic determinants assembled into a high molecular weight carrier. A good immunogen should also have the maximum number of epitopes exposed. These requirements can be difficult to achieve by random chemical coupling of antigens to a carrier. An ideal situation would be where the antigen was presented in the correct conformation on the surface of a large particular complex. Furthermore the particular nature of such a system would facilitate the purification of the antigen by simple physical means.

These requirements are rarely achieved by the simple synthesis of monomeric proteins by recombinant DNA technology or chemical synthesis.

Prior to the present invention, the only self-assembling, particular antigen presentation system for production of immunogens in yeast was based on the fusion of antigens (e.g. the Herpes Simplex Virus I (HSV-I) glycoprotein D or a Poliovirus antigen) to the Hepatitis B surface antigen (HBsAg) protein via recombinant DNA technology (Valenzuela et al 1985 Biotechnology 3, 323). These fusion proteins aggregate to form 22 nm particles. This system has serious disadvantages: (1) yields are very low; (2) particles do not form in the yeast cell but are a by-product of the extraction process (Hitzeman et al 1983 Nucl. Acids Res. 11,27450. This imposes limitations on the production process; (3) some fusions do not form particles; (4) the HBsAg component exerts immunodominance in some cases, i.e. antibodies are made preferentially to HBsAG.

Kniskern et al in *Gene* 46 135 (1986) have reported that Hepatitis B core antigen (HBcAg) forms particles in yeast at very high levels, but there has been no published report of its use to carry other epitopes. As these particles are reported to be highly immunogenic in mice they may exert immunodominance like the HBsAg particles.

A corresponding system in bacteria has been reported by Haynes et al (Bio/Technology 4 637 1986). Tobacco mosaic virus (TMV) coat protein is the entity which assembles into a particular structure. When the TMV coat protein is expressed in *E. coli* and then purified it is possible to assemble the proteins into polyvalent particles in vitro. Fusion proteins made by TMV coat protein and another protein may product hybrid particles that are immunogenic. A polio epitope of only eight amino acids has been tested and shown to be immunogenic although it was four times less immunogenic than the Salk vaccine. This system has the potential advantages that the size of the particle may be varied experimentally and mixed particles (i.e. carrying more than one type of epitope) could possibly be easy to produce. However, an anticipated disadvantage is that only relatively small antigens will be able to be added to the TMV particle.

Mellor et. al. in Nature 313 243 (1985) disclose a fusion protein comprising the product of a yeast Ty open reading frame ORF1 (now designated the TYA gene), an open reading frame ORF2 (now designated the TYB gene) and nucleic acid coding for interferon. However, there is no disclosure or suggestion in this paper that the fusion proteins produced, or indeed any Ty protein, are or might be capable of assembling into particles.

DISCLOSURE OF THE INVENTION

It has now been discovered that certain proteins expresses by the genetic material of tetrotransposons have the ability of self-assembling into particles. It has also been discovered that it is possible to construct fusion proteins, based on such retrotransposon-derived assembling proteins, which can assemble into antigen- (or other biologically active molecule-) presenting particles. A further discovery that has been made is that similar fusion proteins can be constructed based on assembling proteins from RNA retroviruses.

According to a first aspect, the present invention provides a fusion protein capable of assembling into a particle, the fusion protein comprising a first amino acid sequence and a biologically active second amino acid sequence, wherein the first amino acid sequence is substantially homologous with a particle-forming protein encoded by a retrotransposon or and RNA retrovirus and wherein, if the second amino acid sequence contains more than thirty amino acid residues, the first thirty residues of the second amino acid sequence do not form an amino acid sequence naturally directly fused to the first amino acid sequence by the said retrotransposon or RNA retrovirus.

According to a second aspect, the invention provides a particle comprising a plurality of fusion proteins, each fusion protein comprising a first amino acid sequence and a second amino acid sequence, wherein the first amino acid sequence is substantially homologous with a particle-forming protein encoded by a retrotransposon or an RNA retrovirus and wherein the second amino acid sequence is biologically active and not naturally fused to the first amino acid sequence by the said retrotransposon or RNA retrovirus.

Such particles will generally be substantially pure, by which is meant at least 5%, 10%. 20%, 50%, 80%, 90%, 95% or 99% by weight pure, in increasing order of preference.

A given particle may be composed of a plurality of different fusion proteins; that is to say fusion proteins having different second amino acid sequences from each other. Two, three or even more different second amino acid sequences may be present in a particle.

The first amino acid sequence may be the product of the yeast Ty TYA gene, the product of copia and copia-like elements from insects or the gag gene of RNA retroviruses.

Retrovirusus include Human Immunodeficiency Virus I and II (HIV-I, HIV-II), SIV, Human T-cell Lymphotrophic Virus I and II (HTLV-I, HTLV-II). Murine Leukaemia Virus, Moloney Murine Leukaemia Virus, Mouse Mammary Tumour Virus, Avian Leukosis Virus, Feline Leukaemia Virus, Human B-cell Lymphotrophic Virus, and Bovine Leukaemia Virus. Retrotransposons, as indicated above, include the Ty element of yeast, the and copia-like copia elements of insects such as *Drosophilia melanogaster*, VL30 in mice and IAP genes in mice.

Preferred retrotransposon include the yeast retrotransposon Ty. It has previously been shown that Ty directs the synthesis of 60 nm virus-like particles (Ty-VLPs) (Mellor et al 1985a Nature 318, 513). It has now been discovered that the p1 protein, encoded by the TYA gene is stable and does not appear to require further processing. Therefore the Ty-encoded amino acid sequence is preferably the p1 protein encoded by the TYA gene. It is known (Fulton et al NAR 13(11) 1985 4097) that both classes (I and II) of Ty make p1; so either class may be used.

The Ty-encoded amino acid sequence need not be the whole of the p1 protein; instead it may be a part of the p1 protein encoded by a part of the TYA gene, which part is capable of directing the synthesis of Ty virus-like particles (Ty-VLPs). It has been determined that a portion of the amino acid sequence 286 to 381 (FIG. 16) is needed for particle formation. Preferably the Ty-encoded amino acid sequence is derivable from Ty1-15. The stop codon at the end of the TYA gene is preferably not included; if it is includes, however, fusion protein may continue to be expressed, albeit at low yield, as it appears that the stop condon may be ignored with a frequency of about 1 in 20 times by the frame shifting mechanism described by Wilson et al (NAR 14(17) 1986 7001).

It is therefore now shown, among other thins, that Ty protein p1, the product of the TYA gene (Dobson et. al. 1984 EMBO.J 3, 1115) and portions thereof containing at least a fraction of the 286 to 381 amino acid sequence in FIG. 16 is sufficient to product Ty-VLPs.

The second amino acid sequence (i.e. in particular embodiments the non-Ty protein coding region) could be any amino acid sequence either known to the art or yet to be elucidated. The biological activity may be a single type of activity (for example antigenicity), receptor biding activity, therapeutic activity or targeting activity (i.e. the ability to home to a particular target) or it may have a combination of two or more different biological activities. Equally, different fusion proteins may assembly into a particulate antigen, thereby causing the whole particle to have more than one activity.

As an example the second amino acid sequence may be derived from a lympholine gene such as an interferon gene, or a gene coding for an antigen of an infectious agent such as a virus, bacterium or other (e.g. protozoal) parasite. For example, it may be an antigen of influenza virus, an HIV-I or HIV-II (i.e. HTLV-III, LAV or AIDS) virus, a rabies virus, FMDA virus, HBsAg, HBcAg, polio virus, influenza virus, parainfluenza virus, respiratory syncytial virus, rhinovirus, coronavirus, adenovirus, Rotaviruses, Norwalkviruses, Arboviruses e.g. Dengue, Herpes simplex, Cytomegalovirus, Epstein Barr virus, Measles virus, Mumps virus, Rubella, Equine influenze virus, Equine rhinopneumonitis, Swine transmissible gastroenteritis virus, Distemper, Parovovirus, FeLV, Venezuelan or Western equine encephalitis, plasmodium trupanosome, Schistosomes, Chlamydia trachomatic or a meningococcus or it may be a fragment of the above antigens or a peptide resulting from a chemically synthesized coding sequence such that the resulting peptide has substantially the same antigenicity of the above antigens or fragments thereof.

The nucleotide sequence for a wide variety of viral and bacterial antigens are known such that the antigen can be prepared by recombinant DNA techniques. These DNA coding sequences can be used to code for the second amino acid sequence of the fusion protein of the present invention. For example, the nucleotide sequence for antigen related to common diseases such as whooping cough and malaria are known. Whooping Cough, Bordatella pertussis, WO 87/03301, June 4, 1987; Malaria Plasmodium vivax and P. falciparum, Dame, et al., *Science,* 225:593, 1984; Enea, et al., *Science,* 225:628, 1984; Young, et al., *Science,* 225:958, 1984. Other common diseases for which antigen nucleotide sequence are known as: Hepatitis, EPO 218,474 and EPO 020,251; Herpes, EPO 216,195 and Japan 61-97630; Rabies, WO 87/00179; Chickenpox, EPO 210,931; and Polio, WO 86/01828 and Japan 61-47585.

A first part of the second amino acid sequence may be a linker sequence, which may in some circumstances be readily cleavable. The remainder of the second amino acid sequence may thus be cleaved off in a purification step.

Particulate antigens in accordance with the invention are therefore useful in the preparation of vaccines, which form a further aspect of the invention. The second amino acid sequence may thus code for an amino acid sequence of an antigen of one of the above infectious agents. The vaccine comprises a particulate antigen and a physiologically acceptable non-toxic carrier, such as sterile physiological saline or sterile PBS. Sterility will generally be essential for parenterally administrable vaccines. One or more appropriate adjuvants may also be present. Examples of suitable adjuvants include muramyl dipeptide, aluminum hydroxide and saponin.

It should be noted that vaccines in accordance with the invention may present more than one antigen. Either a cocktail of different particulate antigens may be used, or a homogeneous population of particulate antigens having more than one epitope could be used (prepared, for example, by allowing a mixture of different hybrid proteins to aggregate into particles or by expressing more than one particulate antigen in the same cell); alternatively, a vaccine could contain a mixture of these sorts of particulate antigens.

In a further aspect, the invention provides nucleic acid comprising a first nucleotide sequence and a second nucleotide sequence, wherein the first nucleotide sequence is substantially homologous with or complementary to genetic material in a retrotransposon or RNA retrovirus encoding a particle-forming protein, and wherein the second nucleotide sequence encodes, or is complementary to a nucleotide sequence which encodes, another, biologically active, amino acid sequence, the nucleic acid being capable of being expressed in a single reading frame to form a fusion protein which is not naturally produced by the said retrotransposon or RNA retrovirus and which fusion protein assembles into a particle.

It will generally be the case that the nucleic acid will be capable of being expressed without splicing or antitermination events. There will generally be no frameshifting.

In certain embodiments of the invention, we provide a TYA gene derivative that can be fused to any non-Ty protein coding sequence to produce a TYA fusion gene. The TYA fusion gene produces a fusion protein that assembles into hybrid Ty-VLPs. These hybrid Ty-VLPs constitute a high molecular weight particulate antigen (or other particle) presentation system that can be produced in very high yields and that can be purified by simple physical procedures.

Further according to the present invention we provide an expression vector including nucleic acid as defined above. An example is pMA5620, which includes the TYA gene derivative, and which directs the high level production of hybrid Ty-VLPs in yeast.

Expression vectors in accordance with the invention will usually contain a promoter. PGK is a preferred promoter, but any other promoter may be used if necessary or desirable. Examples includes GAPD, GAL1-10, PHO5, ADH1, CYC1, Ty delta sequence, PYK and hybrid promoters made from components from more than one of these promoters or any other promoter.

The invention also includes host cells for example, bacterial cells, such as E. coli, yeast cells such as Saccharomyces Cerevisiae, or animal cells such as Chinese Hamster Ovary cells (CHO) or COS cells containing the above expression vectors that direct production of hybrid particles.

Because of the polyvalent nature of the particulate antigens it is likely that it will be easier to product antibodies than with conventional antigens and that those antibodies will have specific characteristics. The invention thus further provide antibodies raised against particles of the invention which are antigenic. The antibodies may be polyclonal (obtained for example by injecting antigens into a rabbit) or monoclonal antibodies, produced by bybridoma cells in accordance with the invention. Because of the polyvalent nature of the particulate antigens it is likely that in vitro immunization can be achieved more readily than with other forms of antigen; this may facilitate the production of human monoclonal antibodies. Hybridoma cells may be prepared by fusing spleen cells from an immunized animal with a tumor cell. Appropriately secreting hybridoma cells may thereafter be selected. (See Koehler & Milstein *Nature* 1976 296 495).

The invention also provides a suitable technique for purifying biologically active peptides. This aspect of the invention is based on the fact that it is generally relatively easy to separate particles from associated impurities, for example, by filtration or centrifugation. Therefore, there is also provide a method of producing a substantially pure biologically active peptide the method comprising separating particles as described above from associated impurities and subsequently cleaving biologically active peptide from the fusion proteins of the particles.

Fusion protein and particulate antigens of this invention are useful as diagnostic reagents. Particulate antigens for diagnostic purposes are particularly advantageous because they can be physically separated by centrifugation or filtration and can be directly dispersed on solid supports such as glass or plastic slides, dip sticks, macro or micro beads, test tubes, wells of microtiter plates and the like. The particulate antigens of this invention may also be dispersed in fibrous or bibulous materials such as absorbent disc (see U.S. Pat. No. 4,632,901), strips or chromatography columns as the solid support. The particles and fusion proteins readily adhere to solid supports. The particles may after purification be disrupted into fusion proteins and the fusion protein may be dispersed on surfaces as indicated above. These reagents are useful for a variety of diagnostic tests. For example, a test sample suspected of having antibody to the particular antigen and a fluorescent, enzyme or radio-labeled antibody is competitively reacted with the particulate antigen or fusion protein on a solid support and the amount of labeled antibody which binds to the particulate antigen on the solid support. Particulate antigens of this invention are also useful for agglutination reactions with antibodies. Those skilled in the diagnostic arts will recognize a wide variety of application of particulate antigen and fusion protein of this invention for diagonstic purposes.

The invention is now illustrated by the following Examples, with reference to the accompanying drawings, in which.

FIG. 4A-C shows photographs of SDS-polyacrylamide gel analyses of fractions from a sucrose gradient separation of particles and proteins from MD40-4c containing pMA91-11, pMA91 and pMA5620-8.

Figure 5:
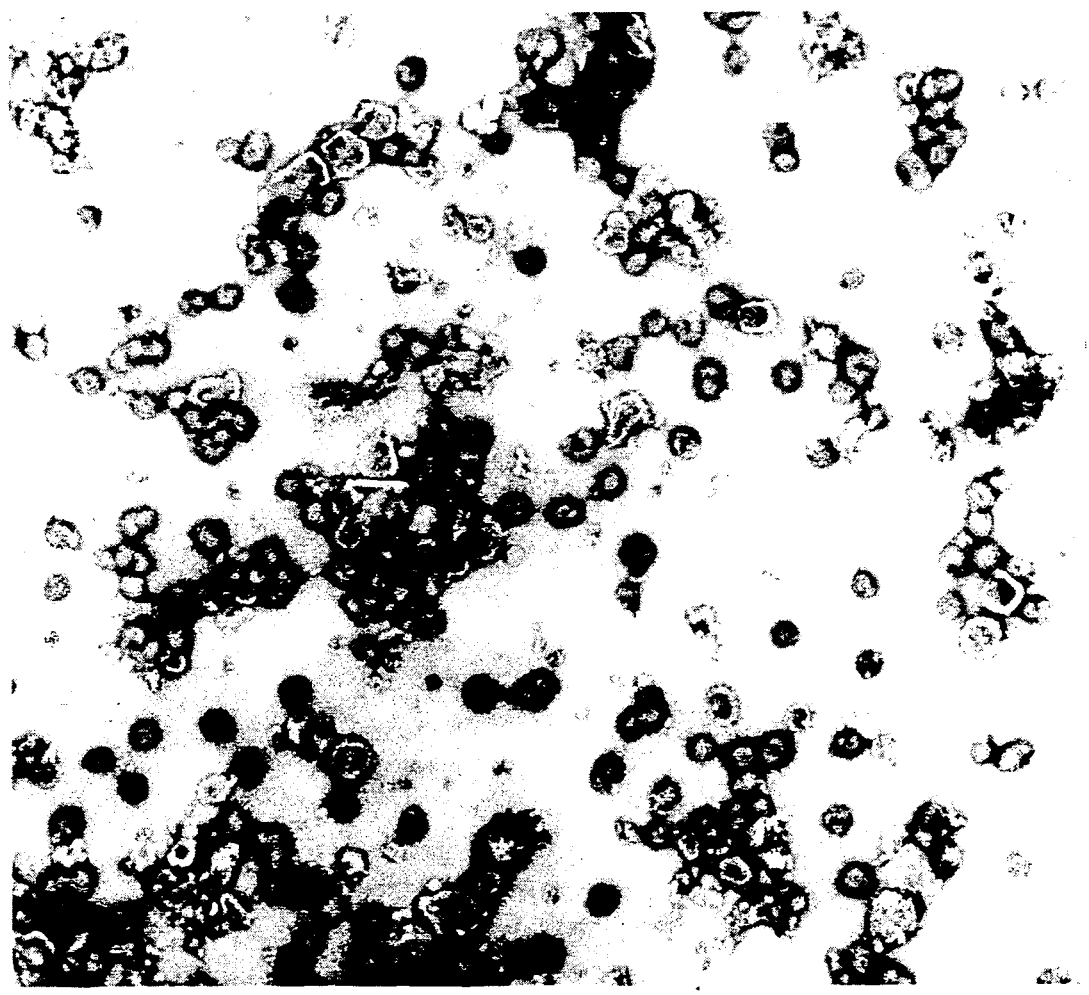

FIG. 5 is a photograph of hybrid Ty:IFN-VLPs purified from MD40-4c containing pMA5620-8.

Figure 6A:

FIG. 6A&B shows photographs of Western blots of the sucrose gradient fractions from extracts of MD40-4containing pMA5620-8. (a) Shows the result using anti Ty-VLP antibody; (b) shows the results using anti interferon antibody.

Figure 7:
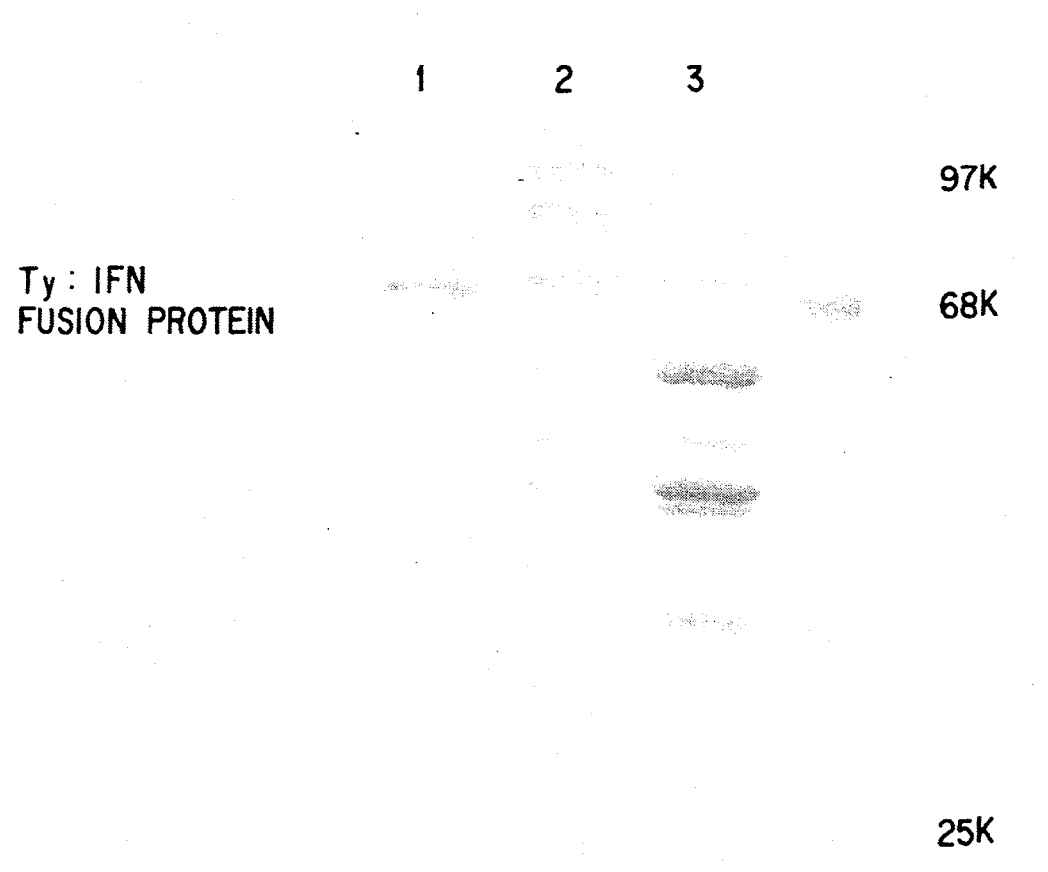

FIG. 7 shows a photograph of Coomassie stained SDS polyacrylamide gel analyses of proteins in the purified hybrid Ty:IFN-VLP preparation (1) and total extracts of MD40-4c transformed with pMA5620-8 (2) and untransformed MD40-4c (3).

FIG. 8A-D shows photographs of Western blots using anti Ty-VLP antibody (b), anti hybrid Ty:IFN-VLP antibody (d) and the corresponding 'prebleed' sera (a+c). Each is used against total extracts of MD40-4c containing pMA91 (1) and pMA91-1 (2). Plasmid pMA91-1 directs the synthesis of IFN-alpha2. pMA91 is a negative control, producing no interferon.

FIG. 9 shows the nucleotide sequence of the 262 bp SpeI:SpeI fragment containing HA codons 25-111. referred to in Example 5.

Figure 10:
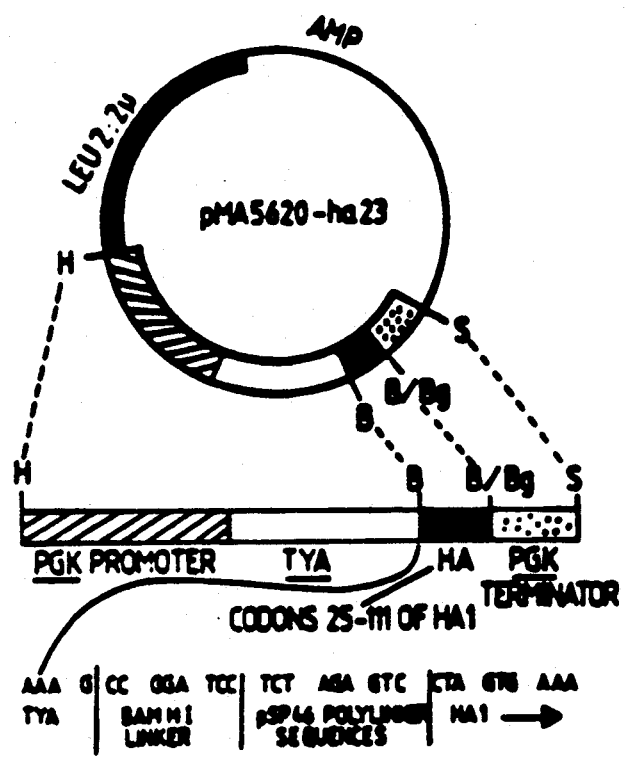

FIG. 10 shows a diagram of plasmid pMA5620-ha23.

Figure 11A:
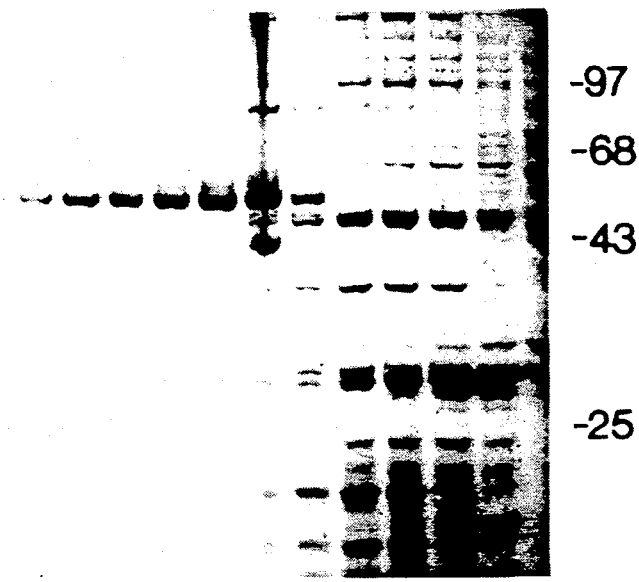

FIG. 11A&B shows an SDS-PAGE analysis of sucrose gradient fractions of extracts of MD40-4c transformed with pMA5620 or pMA5620-ha23. Proteins are stained with Coomassie blue.

Figure 12:
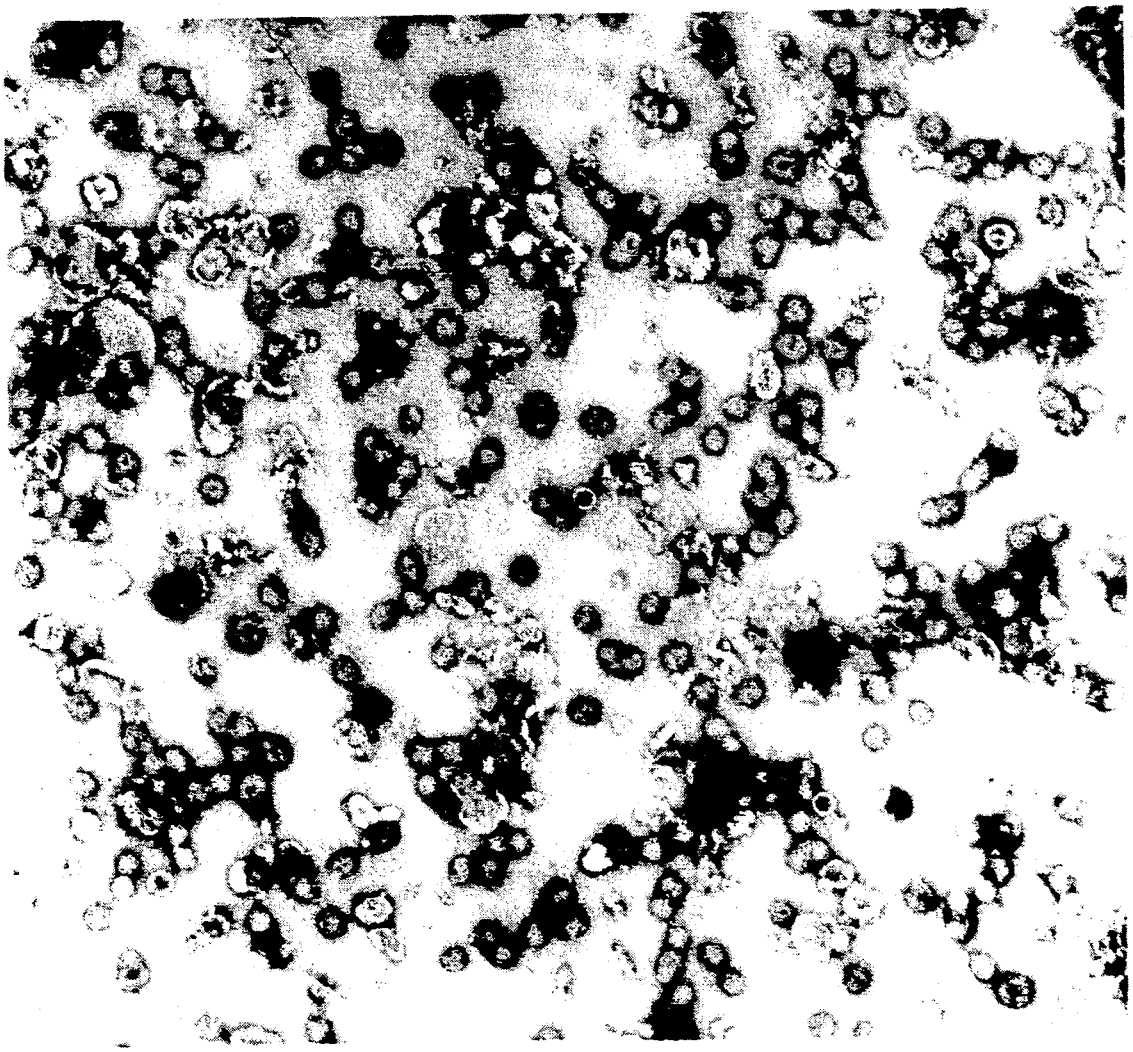

FIG. 12 shows an electron micrograph of purified Ty:HA-VLPs.

Figure 13A:
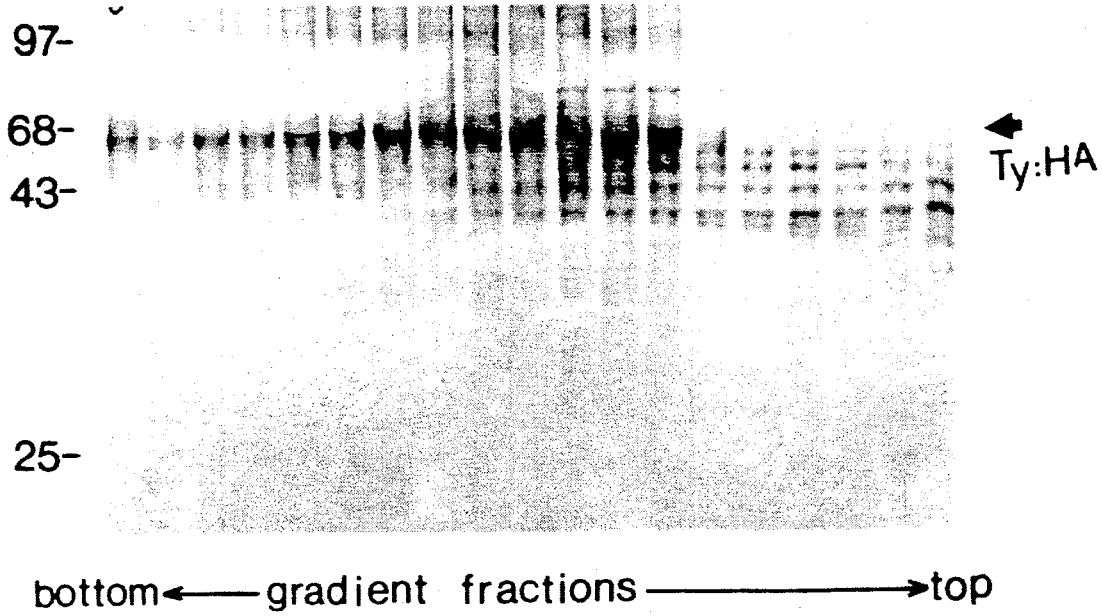

FIG. 13A&B shows Western blots of proteins from sucrose gradient fractions of extracts of MD40-4c transformed with pMA5620-ha23. Blots were probed with anti- Ty-VLP antibody and anti-whole influenza virus antibody.

FIG. 14A-E shows Western blots of purified Ty:HA-VLPs, whole influenza virus NT60 (H3) and whole influenza virus PR8 probed, from left to right, with normal 'pre-bled' rabbit serum, anti-Ty-VLP antiserum, normal 'pre-bled' rabbit serum, anti-Ty:HA-VLP antiserum and anti-whole influenza virus serum.

Figure 15:
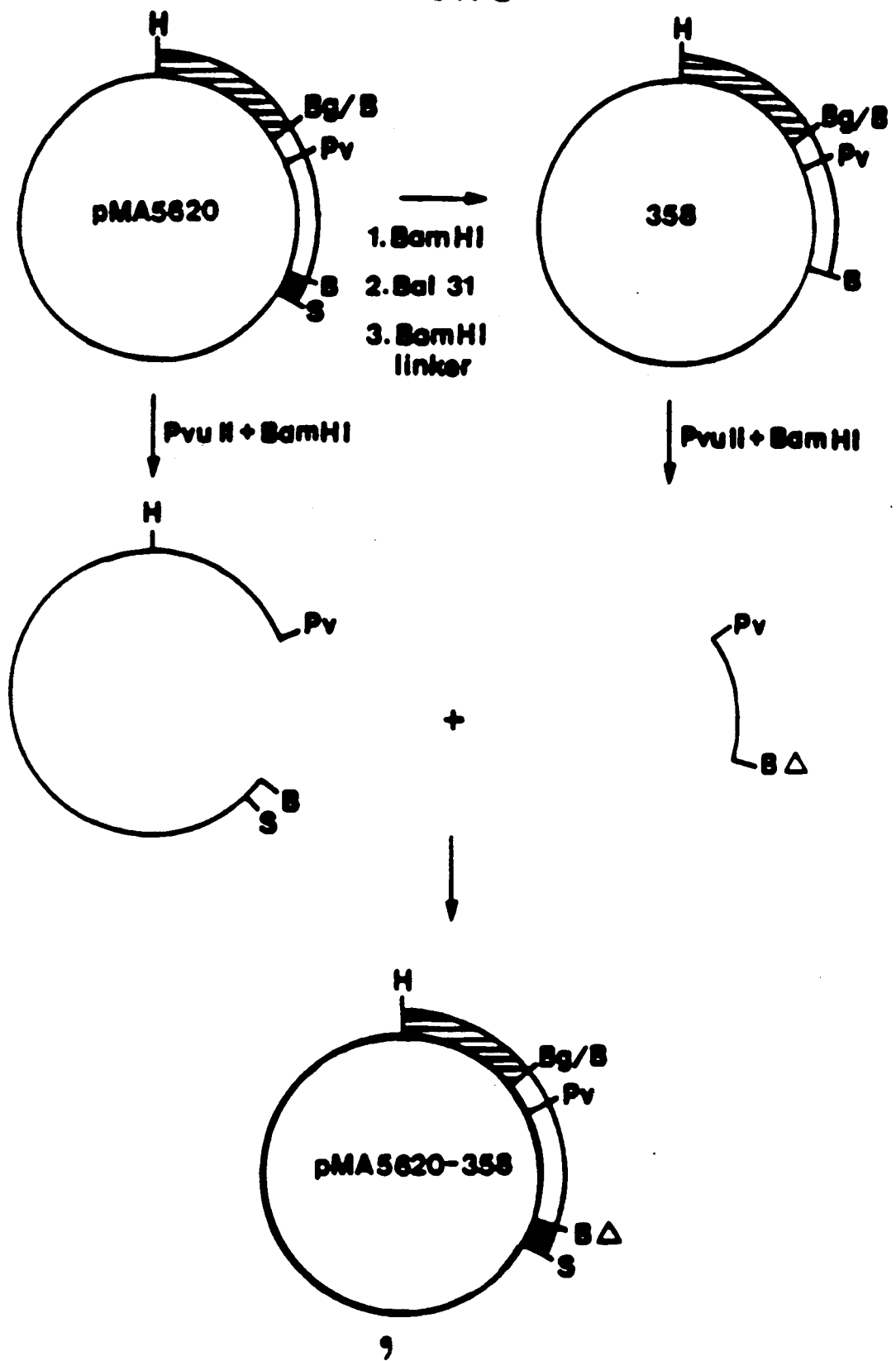

FIG. 15 shows the strategy for preparing pMA5620-358 from pMA5620. pMA5620-358 contains the first 280 codons of TYA.

FIG. 16 shows the DNA and amino acid sequence of TYA 1 through 381 amino acids which contains the 286 through 381 segment at least a portion of which is needed for particle formation. Symbols for amino acids are:

| Amino Acid | One-letter Symbol |
|---|---|
| Alanine | A |
| Arginine | R |
| Asparagine | N |
| Aspartic acid | D |
| Asn and/or Asp | B |
| Cysteine | C |
| Glutamine | Q |
| Glutamic acid | E |
| Gln and/or Glu | Z |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

EXAMPLE 1

Strains used were *E. coli* AKEC28 (C600, thrC, thyA, trpC1117, hsdRK, hsdK) and *S. cerevisiae* MD40-4c (urd2, trp1, leu2-3, leu2-112, his3-11, his3-15). *E. coli* media were prepared according to Miller (miller 1972 Experiments in Molecular Genetics, CSH p433) and yeast media were prepared according to Hawthorne and Mortimer (Hawthorne and Mortimer 1960 Genetics 45, 1085).

*E. coli* was transformed using standard methods (Maniatis et al. 1982 Molecular Cloning—A Laboratory Manual, CSH p199). Yeast was transformed as described by Hinnen et al. (Hinnen et al. 1978 Proc. Natl. Acad. Sci. 75, 1929).

Standard procedures were used for restriction digestion and plasmid constructions (Maniatis et al. 1982 op. cit.). Restriction enzymes and T4 DNA ligase were used according to the suppliers' instructions. Bal 31 exonuclease digestions were carried out as described by Dobson et al. (Dobson et al. 1982 Nucl. Acids Res. 10, 5463). Deletion end points were determined by DNA sequencing (Sanger et al. 1977 Proc. Natl. Acad. Sci. 74, 5463). BamHI synthetic oligonucleotide linkers were obtained from Pharmacia.

Plasmid DNA was isolated from *E. coli* preparatively as described by Chinault and Carbon (Chinault and Carbon 1979 Gene 5, 111) and for rapid analysis by the methods of Holmes and Quigley (Holmes and Quigley 1981 Anal. Biochem. 114, 193).

Ty-VLPs were purified as follows: Yeast cells were grown selectively at 30° C. to a density of $8 \times 10^6$ cells.ml$^{-1}$. The cells were then collected by low speed centrifugation, washed once in ice-cold water and resuspended in TEN buffer (10mM Tris, pH 7.4; 2 mM EDTA; 140 mM NaCl) at 1 ml per 1 liter of cells. The cells were disrupted by vortexing with glass beads (40-mesh;BDH) at 4° C. until >70% were broken. The beads were pelleted by low speed centrifugation, then the supernatant was collected and the debris removed by centrifugation in a microfuge for 20 minutes. The Ty-VLPs were then pelleted from the supernatant by centrifugation at 100,000 g for 1 hour at 4° C. and by resuspending overnight in TEN buffer. The resuspended Ty-VLPs were centrifuged in a microfuge for 15 minutes at 4° C. to remove cell debris prior to loading the supernatant onto a 15-45% (w/v) sucrose gradient in 10 mM Tris, pH 7.4; 10 nM NaCl and spinning at 76,300 g for 3 hours at 15° C. Fractions were collected through the bottom of the tube and the peak fractions were identified by running aliquots of the fractions on SDS-PAGE gels and Coomassie blue staining. VLPs were concentrated by centrifugation of the peak fractions at 100,000 for 1 hour at 4° C.

Protein extracts of whole yeast cells were prepared as previously described (Mellor et al. 1983 Gene 24, 1). Gel procedures were those of Laemmli (Laemmll 1970 Nature 227, 68). Protein concentrations were measured by a dye-binding assay (Bradford 1976 Anal. Biochem. 72, 248) obtained from Bio-Rad Laboratories.

A polycolonal horse anti-interferon (IFN)-alpha antibody was purchased from Boehringer Mannhein. Anti-Ty-VLP antisera were prepared in rabbits by standard procedures.

Western blotting was carried out as described by Towbin et al. (Towbin et al. 1979 Proc. Natl. Acad. Sci. 76, 4350). Bound antibody was detected using either a rabbit anti-horse second antibody conjugated to horseradish perosidase (Miles Scientific) or a goat anti-rabbit second antibody followed by a peroxidase-antif-peroxidase (PAP) complex raised in rabbit (Sigma). The enzymatic reaction was developed as described by De Blas and Cherwinski (De Blas and Cherinski 1983 Anal. Biochem. 133, 214).

Plasmid, pMA91-11, has been described previously (Dodson et al 1984 EMBO.J. 3, 1115): it contains the first 1450 nucleotides of the major transcriptional unit of the Typ element, Ty1-15, inserted into the high efficiency expression vector pMA91 (Mellor et al. 1983 op. cit; Kingsman and Kingsman 1985 Biotech. and Genet. Eng. Rev. 3, 377). The Ty component was derived from pKT40b as described by Dobson et al. (op. cit); pKT40b has been deposited with the National Collection of Industrial Bacteria, Aberdeen, U.K. under accession number NCIB 12427. In turn, the expression vector pMA91 consists of plasmid pBR322 sequences which allow replication and selection in *E. coli*, the yeast 2 micron plasmid origin or replication, which allows efficient autonomous replication in yeast, the yeast LEU2 gene as a selectable marker in both yeast leu2 and *E. coli leuB* mutants and a Bg/II expression site which separates the upstream non-coding region of the yeast PGK gene from −15000 to −1 from the 3' region of PGK which contains all the signals for yeast transcription termination. Plasmid pMA91 is also described in U.S. Pat. No. 4,615,974, although it should be carefully noted that the plasmid designated as pMA3013 in FIG. 15 of this U.S. patent is what is now known as plasmid pMA91. The plasmid shown in the lower part of FIG. 1 of U.S. Pat. No. 4,615,974 has since been renamed.

Figure 1:
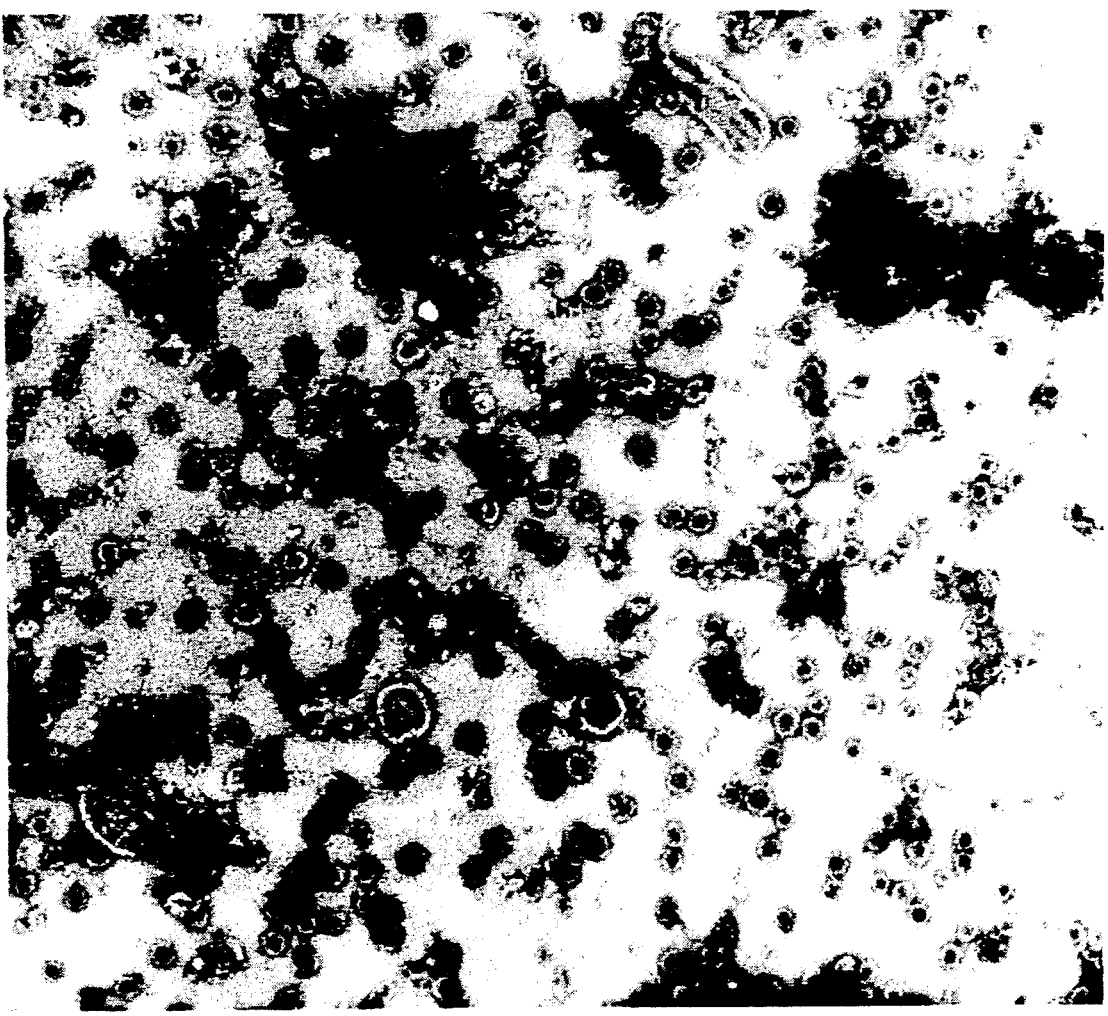
FIG. 1 is a photograph of Ty virus-like particles (Ty-VLPs) purified from MD40-4c transformed with plasmid pMA91-11.

Ty expression is driven, thereof, from the promoter of the highly efficient yeast phosphoglycerate kinase gene (PGK) and yeast extracts of strains containing pMA91-11 overproduce massive amounts of p1 protein, the primary translation product of the TYA gene (Dobson et al. 1984 op. cit; Mellor et al. 1985a op. cit). We now demonstrate that extracts of yeast transformants containing pMA91-11 contain Ty-VLPs in large quantities (FIG. 1). Therefore, TYA alone contains sufficient information to make Ty-VLPs and the p1 protein found in extracts of MD40-4C containing pMA91-11 is assembled into particles (FIGS. 1 and 4). This information provides the basis for the present invention.

Figure 2:
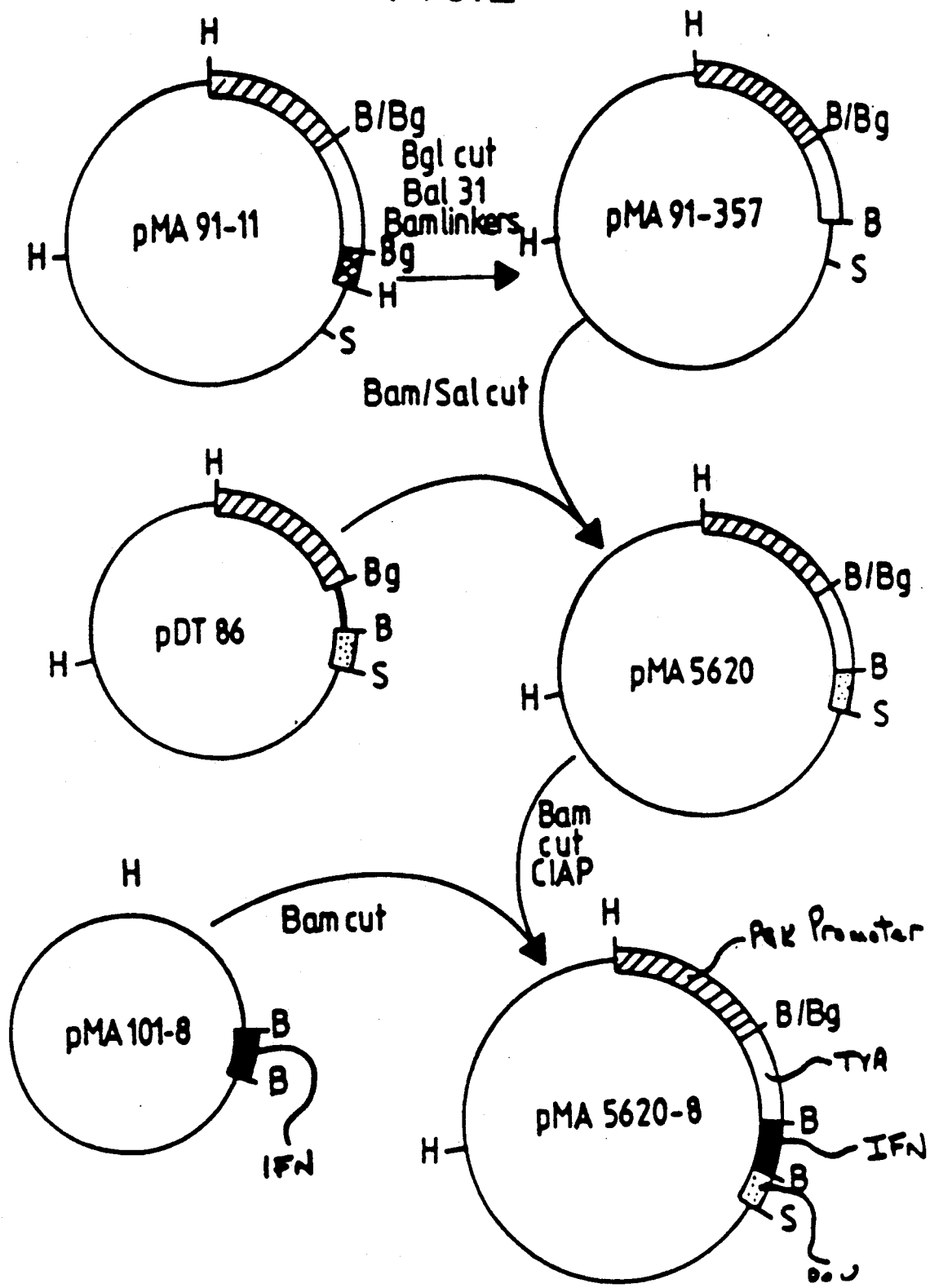
FIG. 2 is a schematic diagram of the construction of pMA5620 and pMA5620-8.

The constructions of a plasmid vector, pMA5620, that would direct the synthesis of any hybrid Ty-VLP particle is shown schematically in FIG. 2. This required the construction of a vector containing a convenient restriction endonuclease site within the TYA gene such than any coding sequence can be inserted into that site to create a TYA hybrid gene. However, it is essential that within such a hybrid there is sufficient TYA coding sequence to direct the synthesis of Ty-VLPs.

Figure 3:
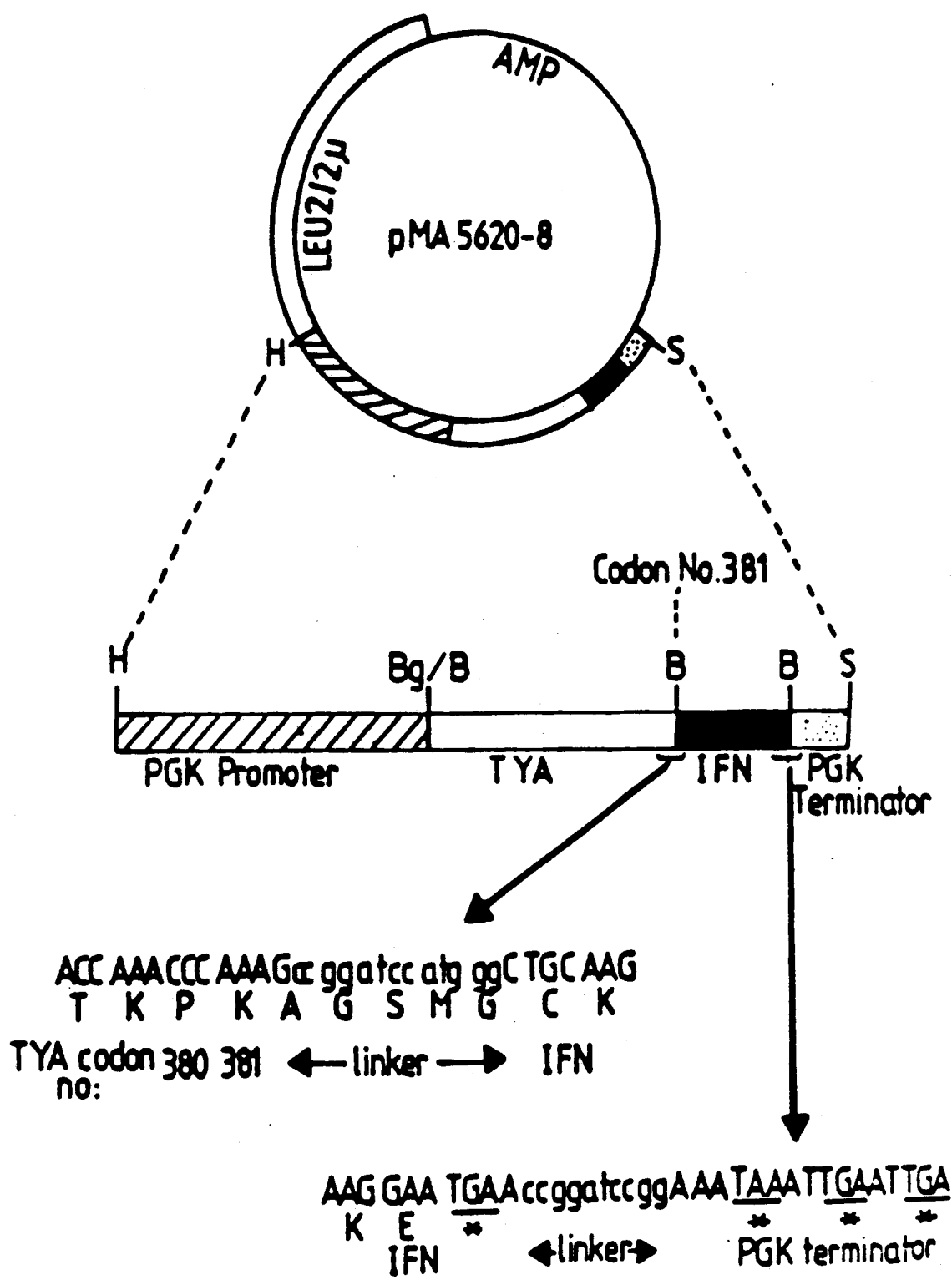
FIG. 3 is a schematic diagram of plasmid pMA5620-8, with an expanded diagram of the key components of this example of the invention and the nucleotide sequences of key junctions.

Plasmid pMA91-11 was cleaved with BglII, digested with Bal 31 exonuclease for various times and re-ligated in the presence of excess Bam HI linkers (CCFFATCCGG). The deletion end points of the resulting plasmids were determined by DNA sequencing. Plasmid pMA91-537 is a deletion derivative in which 265 bp have been removed. This places the BamHI linker one nucleotide beyond condon 381 of TYA (FIG. 3).

In order to provide both transcription termination sequences and translation stop codons in all three reading frames the deleted PGK 3' terminator sequences of pMA91-357 were replaced with a 287 bp BamHI-SalI DNA fragment isolated from plasmid pDT86. This DNA fragment is a modified 3' transcription terminator fragment from the yeast PGK gene which contains translation stop codons in all three reading frames downstream of the BamHI site (FIGS. 2 and 3). This terminator fragment starts with a BamHI linker (CCGGATCCGG) linked to the last sense codon of the PGK coding sequence and extends to the HindIII site 279 nucleotides beyond the PGK coding sequence (Hitzeman et al. 1982 Nucl. Acids Ted. 10, 7791). In these constructions the HindIII site has bee converted to a SalI site using a synthetic linker. The terminator fragment is not critical and any fragment containing termination codons in all three reading frames followed by yeast transcription terminator would suffice. The resulting plasmid, pMA5620, contains a unique BamHI site into which any suitable sequence can be inserted to produce a hybrid protein which will be assembled into hybrid Ty-VLPs.

In order to test pMA5620 an interferon-alpha2 (IFN) cDNA was used as a model antigen coding sequence. A 540 bp BamHI IFN-alpha2 cDNA fragment, designated fragment 8 (Mellor et al. 1985b Gene 33, 215) was inserted into the unique BamHI site of plasmid pMA5620. The resulting plasmid is designated pMA5620-8 (FIGS. 2 and 3).

Figure 6B:
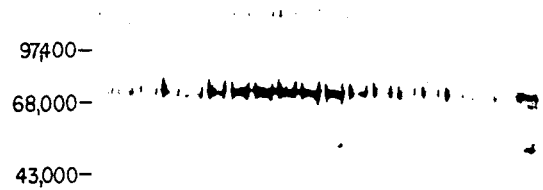

VLPs were prepared from yeast strain MD40-4c transformed with plasmid pMD5620-8 and fractions from a 15-45% sucrose gradient were run on an SDS-PAGE gel. The proteins in the gradient were visualized by Coomassie blue staining (FIG. 4). The position in the gradient of the predicted 70 kd TYA-IFN fusion protein demonstrated conclusively the particulate nature of the protein. Electron microscopy of the fractions confirmed that particles were present (FIG. 5). In order to establish that this 70 kd particulate protein was indeed a Ty(50 kd):IFN(20 kd) fusion protein fractions from sucrose gradients were again run on SDS-PAGE gels and the separated proteins were transferred to nitrocellulose filters. One filter was probed with a Ty-VLP antibody known to react with Ty proteins and another was probed with an anti-IFN-alpha antibody (FIG. 6). In both cases the 70 kd protein reacted strongly, indicating that this protein contained both Ty and IFN epitopes.

The efficiency of the method for purification of hybrid Ty:IFN-VLPs is illustrated in FIG. 7. The 70 kd hybrid protein is by far the major species in the preparation.

In order to test the efficacy of these hybrid Ty:IFN-VLPs in eliciting an immune response to the model antigen, interferon, an antiserum was raised in rabbits against concentrated hybrid Ty:IFN-VLPs purified from yeast extracts transformed with pMA5620-8. An extract of MD40-4c transformed with plasmid pMA91-1 which over produces IFN-alpha2 (Mellow et al. 1985b op. cit.) was run on an SDS-PAGE gel along side an extract of MD40-4c transformed with pMA91 which produces no interferon. The separated proteins were transferred to nitrocellulose and probed with either Ty-VLP antisera or Ty:IFN-VLP antisera (FIG. 8). Whereas both antisera reacted with Ty proteins present in the extracts only the anti hybrid Ty:IFN-VLP antisera reacted with the 20 kd IFN protein in the extract containing plasmid pMA91-1.

These data show: (1) pMA5620-8 directs the synthesis of a hybrid fusion protein composed of the first 381 amino acids of Ty protein p1 and a non-Ty protein. In this case interferon-alpha2; (2) this fusion protein forms hybrid Ty:IFN-VLPs; (3) the hybrid Ty:IFN-VLPs can be isolated easily; (4) the hybrid Ty:IFN-VLPs present the model antigen, interferon-alpha2, to the rabbit immune system. It is reasonable, therefore, to expect that pMA5620 will direct the synthesis of any hybrid Ty-VLP and that any antigen present in such a particle will be presented to any mammalian immune system e.g. rat, hamster, dog, cat, cattle, sheep, pigs and human. Clearly the interferon cDNA used as an example here could be replaced with any other piece of DNA that would encode a complete protein or part of a protein.

The particulate nature of this antigen presentation system and the ease with which the hybrid Ty-VLPs can be purified make this invention useful as a means of stimulating the production of antibodies to defined antigens, as a means of creating new vaccines, as a means of preparing defined antigens for monoclonal antibody production, as a means of preparing antigens for use in diagnostic assay methods.

Hybrid Ty:IFN-VLPs can therefore be used to raise anti-IFN antibodies (either monoclonal or polyclonal, but preferably monoclonal), which may then be used for the purification of IFN.

EXAMPLE 2

The copia element of *Drosophilia melanogaster* is remarkably similar to the Ty element of yeast in both genetic organization and virus-like particle formation (Mount & Rubin 1985 Mol. Cell. Biol. 5 1630). The region of copia that is equivalent to TYA is called gag by analogy with retrovirus organization. Therefore expression at high levels of the gag region of a copia element in an insect cell expression system may be found to lead to proteins which assemble into particles similar to the Ty-VLPs. If the gas is fused to the coding sequence of another protein the resulting fusion protein may also be found to assemble into a hybrid copia particle analogous to the Ty:IFN hybrid particles described above.

In order to establish copia particles as an antigen presentation and purification system gas from plasmid pPW220 (Potter & Brosein 1979 Cell 17 415) is manipulated by standard recombinant DNA procedures for insertion into a typical high efficiency Baculovirus expression vector such as pAc373 (Smith et al. 1983 J. Virol. 46, 584) to produce plasmid pAc373-gag. Expression is driven by the polyhedrin promoter. An interferon cDNA is then inserted, in frame, into the 3' end of gas to produce plasmid pAc373-gag-IFN. This plasmid is directly analogous to pMA5620-8 (see Example 1 above). pAc373-gag-IFN is then introduced into the Baculovirus, Autographa californica nuclear polyhedrosis virus (AcNPV) by in vivo recombination in *Spodopetra fugiperda* cells (Smith et al. 1983 Mol. Cell. Biol. 4 2156). Recombinant viruses are harvested from occulsion-minus plaques and used to reinfect fresh *S. frugiperda* cells. Hybrid copia:IFN particles are harvested at 72-96 hours post-infection and fractionated on a sucrose gradient to separate then from Baculovirus contamination. Particles are identified by electron microscopy and Western blotting as described for Ty-IFN hybrid particles (see Example 1 above).

EXAMPLE 3

The general procedure of Example 2 is followed, except that a recombinant plasmid containing the gag-IFN fusion expressed by the Brosophila ADH gene promoter (Benyajati et al. 1983 Cell 33 125) is introduced into any insect cell (e.g. Drosophila Schneider 2 cells) by simple DNA mediated transfection.

EXAMPLE 4

The TYA gene of the yeast Ty element is directly analogous to the gag genes of avian and mammalian retroviruses. As the product of the TYA alone is capable of forming particles it is likely that any gag protein will do the same and could therefore act as the basis for an antigen presentation and purification system.

In order to establish retroviral gag proteins as antigens purification and presentation systems the gag gene from HIV-I is manipulated by standard recombinant DNA procedures to be inserted into the yeast expression vector pMA91 and a derivative of the mammalian expression vector pSV2 (Southern and Berg 1982 J. Mol. Appl. Genet. 1 327), which contains a mammalian dhfr cDNA (Kaufman et al. 1985 Mol. Cell. Biol. 5 1750), to produce pMA91-HIVgag and pSV25-HIVgag respectively. An interferon cDNA is then inserted, in frame, into both of these molecules at the 3 end of gag to produce pMA91-HIVgag-IFN and pSV25-HIV-gag-IFN respectively. These molecules are analogous to pMA5620-8 (see Example 1 above). pMA91-HIVgag-IFN is then used to transform yeast strain MD40-4c and pSV25-HIVgag-IFN is used to transfect CHO-dhfr-cells. Stable transformants are propagated and cell extracts prepared and fractionated on sucrose gradients. Hybrid HIVgag:IFN particles are identified by electron microscopy and Western blotting. A described for Ty-:IFN hybrid particles (see Example 1 above).

EXAMPLE 5

The procedure of Example 4 is followed, except that pSV25-HIVgag-IFN is introduced into COS cells (Gluzman et al. 1977 J. Virol. 24 534) and hybrid particles are harvested between 3 and 9 days post transfection.

EXAMPLE 6

In this example we demonstrate that hybrid Ty-VLPs containing part of an influenza virus hemagglutinin (HA) can be produced and that these hybrid Ty:HA-VLPs induce the formation of anti-HA antibodies in rabbits.

The strategy for these experiments was essentially the same as for the production and analyses of the hybrid Ty:IFN-VLPs described in Example 1. MRC12/80 anti-whole influenze virus antibody was obtained from the World Influenza Centre at NIMR, Mill Hill, U.K. and was raised against influenze virus strain A/Scotland/840/74 x A/PR/8/34 (H3N2). A region of the HA coding sequence corresponding to codons 25-111 of the NA1 domain of influenza virus A/Memphis/102/72 (H3N2) was chosen for the formation of hybrid Ty:HA-VLPs on the basis of the data of Wilson et al. (1984 Cell 37, 767). A 262 bp SpeI:SpeI (FIG. 9), corresponding to condons 25-111, was purified from an appropriate digest of plasmid MX29. MX29 is plasmid pAT153 (Twigg and Sherratt, 1980 Nature 282, 216) with an H3 HA cDNA derived from the HA RNA from influenza virus strain A/Memphis/102/72 G:C tailed into the PstI site. The sticky-ends of the SpeI:SpeI fragment were filled-in using DNA polymerase I and then the fragment was blunt-end ligated into the HincII site of plasmid pSP46 to produce pSP46-ha23. pSP46 is a derivative of pSP64 (Promega Biotec) in which the HindIII site of pSP64 has been converted into a BglII site. A BamHI:BglII fragment, designated ha23, was purified from pSP46-ha23. ha23 contains the filled-in 262 bp SpeI:SpeI fragment. Ha23 was then inserted into the BamHI site of pMA5620 to produce mPA5620-ha23 (FIG. 10). This plasmid was then used to transform yeast strain MD40-4C to leucine independence.

Figure 11B:
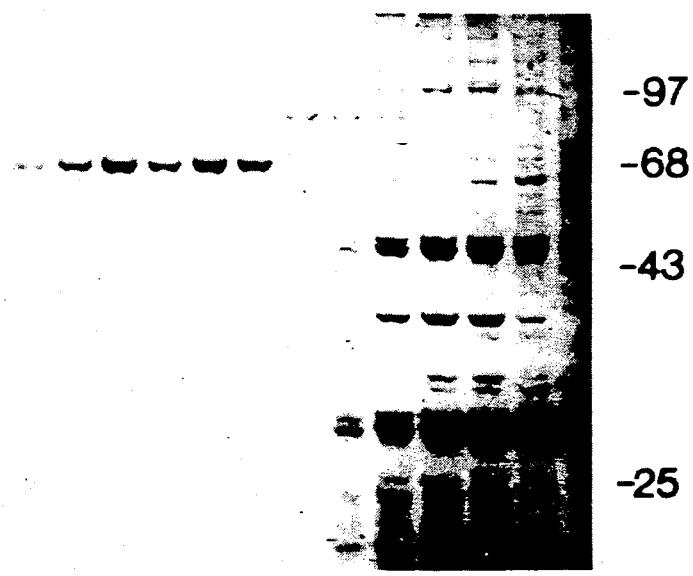

VLPs were prepared from yeast strain MD40-4c transformed with pMA5620-ha23 or pMA5620 and fractionated on a 15-45% sucrose gradient. Fractions were run on an SDS-PAGE gel and proteins were visualized with Coomassie blue (FIG. 11). The position in the gradient of the predicted TYA-HA fusion protein demonstrated the particulate nature of the protein. Electron microscopy of the fractions confirmed that particles were present (FIG. 12).

Figure 13B:
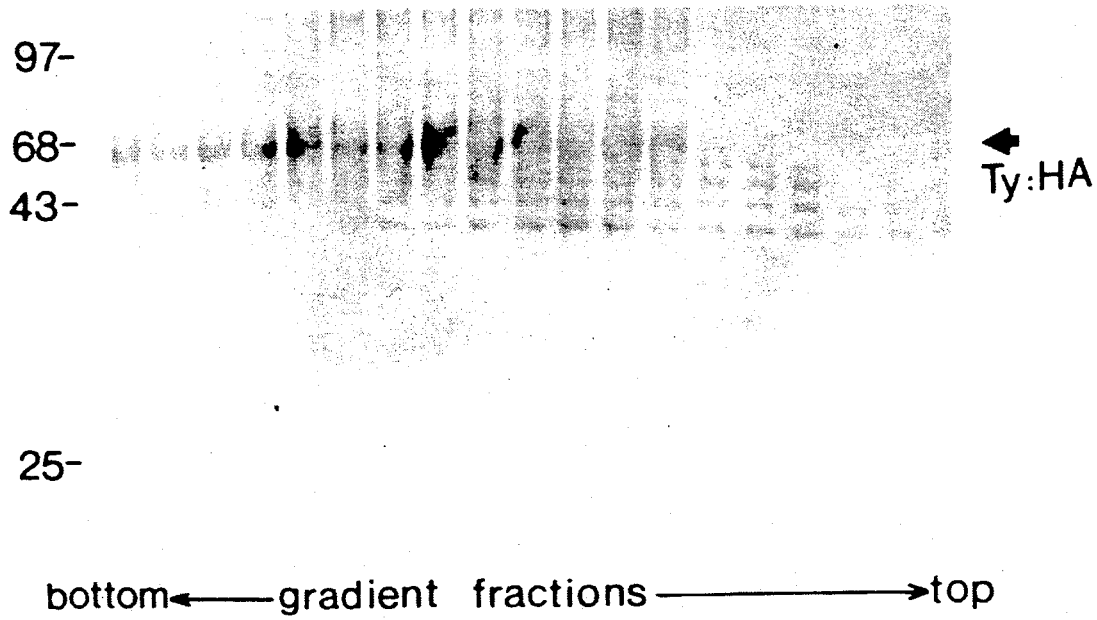

In order to confirm that the particles contained HA antigens fractionated extracts of MD40-4c containing pMA5620-ha23 from similar gradients were again run on SDS-PAGE gels and then separated proteins were electroblotted to nitrocellulose filters. One filter was probed with anti-Ty-VLP antibody known to react with TY proteins and another was probed with anti-HA antibody. In both cases the putative Ty:HA fusion protein reacted strongly indicating that this protein contained both Ty and HA epitopes (FIG. 13).

In order to test the efficacy of these hybrid Ty:HA-VLPs in eliciting an immune response to HA an antiserum was raised in rabbits against concentrated hybrid Ty-HA-VLPs purified from extracts of MD40-4c transformed with pMA5620-ha23. This antiserum was then used to probe proteins from disrupted whole influenze virus by Western blotting. Three protein samples were used. The first was purified Ty:HA-VLPs used to raise the antiserum. The second was whole influenza virus PR8 (H3). The third was whole influenza virus NT60 (H1). Both PR8 and NT60 were obtained from Professor George Brownlee, Sir William Dunn School of Pathology, Oxford, U.K. FIG. 14 shows that the anti-Ty:HA-VLP antibody reacts with the HA1 region of the H3 HA but not with the H1 HA. No such reaction is seen with pre-bled serum nor with anti-Ty-VLP antibody. As a positive control the same samples were probed with anti-whole virus antibody. In this case both H1 HA and H3 HA reacted with the antiserum. The hybrid Ty:HA-VLPs induce the production of anti-HA antibody specific for an epitope for H3 antigen.

These data show that pMA5620-ha23 directs the synthesis of a hybrid fusion protein composed of the first 381 amino acids of Ty protein p1 and a small region of a viral protein, influenze virus HA. This fusion protein forms hybrid Ty:HA-VLPs. The hybrid Ty:HA-VLPs can be isolated easily and present the small HA component to the rabbit immune system in such a way that anti-HA antibodies are produced. These antibodies can distinguish between H1 HA and H3 HA in a Western blot. Clearly the HA component of the hybrid Ty:-HA-VLPs could be replaced with any other influenza virus component or any other virus component and it is reasonable to expect that similar results would be obtained.

EXAMPLE 7

In order to create a series of truncated TYA genes that contained progressively less sequence at the 3′ end, a standard Bal 31 digestion was carried out using pMA5620 as the starting molecule. Plasmid pMA 5620 as cleaved with BamHI, digested with Bal 31 for various times and religated in the presence of excess BamHI linkers (CCGGATCCGG). The deletion end points of the resulting plasmids were determined by DNA sequencing. One of these deletions contains only the first 286 codons of TYA and is designated 358. The deleted PGK terminator sequences of 358 were replaced by ligating the large PvuII-BamHI fragment from pMA5620 with the 680 bp PvuII-BamHI fragment from 358. The resulting plasmid is designated pMA5620–358 (FIG. 15).

Interferon alpha-2 cDNA BamHI fragments with two slightly different 3′ terminal (IFN-8 and IFN-2; Mellor et. al. 1985 Gene 33, 215; Mellor et. al. 1985 Nature 313, 243) were inserted, in frame, into the BamHI sites for pMA5620 and pMA5620-358 to produce plasmids pMA5620-8 and pmA5620-2.

Plasmids pMA91-11, pMA5620 and pMA5620-358 were used to transform yeast strain MD40-4c to leucine independence. The resulting transformants were compared with respect to TYA RNA produced from the plasmids and with respect to the amounts of p1 or truncated p1 proteins, as determined by Western blotting using anti Ty-VLP antibody. The amounts of RNA and protein were the same in each transformant.

Extracts from each transformant were then analyzed by fractionation on 15-45% sucrose gradients follows by Coomassie blue staining for both pMA91-11 and pMA5620 there are p1 or truncated p1 proteins in the region of the gradient that is characteristic of particulate structures. However, in the case of pMA5620-358 no particulate material is observed.

An inteferon alpha-2 cDNA was fused, in frame, to each of the plasmids pMA5620 and pMA5620-358 to produce plasmids pMA5620-8 and pMA5620-358-2. These plasmids were used to transform yeast strain MD40-4c to leucine independent and Ty homologous RNA and p1 and p1:interferon fusion proteins were measured as described above. The levels of RNA and protein are the same for both transformants and also the same as pMA5620. When extracts of yeast transformants containing pMA5620-8 were analyzed on 15–45% sucrose gradients a 70 kD p1:interferon fusion protein was seen in the region of the gradient characteristics of particulate structures. However, no particulate material was seen when extracts containing pMA5620-358-2 were analyzed.

Thus Ty-VLP formation requires at least a portion of the sequence between amino acids 286 and 381. The DNA and amino acid sequence of p1 is shown in (FIG. 16) which also shows the DNA and amino acid sequence of amino acids 286 to 381.

EXAMPLE 8

Example Immunoassay Procedure With VLP Antigen 96-well microtitre plates are coated with VLP antigen (virus like particle with antigen) by incubating 50 μl of 20 μg/ml of VLPs in 50 mM sodium carbonate buffer, pH9.5, in each well for two hours at room temperature. Excess VLPs antigen are washed out of the wells by three, five minute washes with phosphate buffered saline (PBS), pH 7.4. In order to minimize background reactions, the wells are blocked with 100 μl of 2% casein in PBS for one hour at room temperature, followed by three, five minute washes with PBS containing 0.1% Tween-20 (PBS-T). Primary antibody in a test sample is suitably diluted in PBS-T containing 0.5% casein (PBS-CT). A suitable dilution may be a three-fold dilution series from 1/10 to 1/7,290. Primary antibody reactive to the non-Ty component of any hybrid Ty-VLPs, 50 μl of diluted primary antibody is added to the appropriate wells and incubated for two hours at room temperature. Excess primary antibody is removed by three, five minute washes with PBS-T. Secondary antibody is horseradish perosidase-labeled anti-species IgG, and is diluted 1/1,500 in PBS-CT. 50 μl of diluted secondary antibody is added to each well and incubated for two hours at room temperature, followed by five, five minute washes with PBS-T. The substrate is 3,3′,5,5′-tetramethylbenzidine at a concentration of 0.1 mg/ml in 0.1M sodium acetate, adjusted to pH 6.0 with 0.5M citric acid, plus 0.03% hydrogen peroxide. 50 μl of substrate is added to each well and the color reaction developed for 10 minutes. The reaction is terminated by the addition of 25 μl of 0.5M sulfuric acid to each well. Color development is assessed by measurement at 450 nm using a microplate reader. In this way a direct assay of the primary antibody in the test sample is performed.

EXAMPLE 9

Cleavage of Exogenous Protein From Hybrid Ty-VLPs

In situations where hybrid Ty-VIPs are used to purify p1 fusion proteins it is advantageous to remove the p1 component of the fusion protein to leave the exogenous or non-p1 component. This requires cleavage at the junction of the p1 and non-p1 sequence. This provide a means of using Ty-VLPs to produce authentic proteins. One way of achieving this end is to introduce a specific proteolytic cleavage site at the p1/non-p1 junction.

In order to produce non-fusion interferon from Ty-VLPs a derivative of pMA5020, designated pMA5623, was constructed. This is identical to pMA5620 except that at codon 381 of TYA four additional codons are added before the BamHI linker. These codons encode the amino acid sequence Ile-Glu-Gly-Arg which is a cleavage site for the blood coagulation factor Xa (Nagai & Thogersen, 1984, Nature, 309, 810). The junction region for a construction analogous to pMA5620-8, pMA5623-8, is as follows:

```
CCC AAA ATC GAG GGT AGG gga tcc atg ggC TGC AAG
 P   R   I   B   G   R  G  S  M   G   C   K
380 381      Factor Xa                IFN
TYA                      -BamHI
```

When pMA5623-8 is transformed into yeast strain MD40-4c a p1:IFN fusion protein is produced that assembles into hybrid IFN:Ty VLPs. However, in contrast to transformants containing pMA5620-8, incubation of the particulate fusion protein with Bovine Blood faction Xa cleaves the interferon from the particles because of the presence of the cleavage site at the protein fusion junction.

Hybrid IFN-Ty-VLPs are therefore purified from non-particulate proteins by a first round of sucrose density gradient fractionation, as described previously. The IFN is then cleaved off and purified from the particulate p1 protein by a second round of sucrose density gradient fractionation to yield pure "authentic" interferon.

The interferon coding sequence illustrated in this example can be replaced by any other coding sequence and so this strategy can be applied to the expression and purification of any protein.

What is claimed is:

1. A fusion protein comprising a first and second amino acid sequence wherein the first amino acid sequence is encoded for by a yeast TYA gene sequence and the second amino acid sequence is encoded for by a gene sequence which encodes a biologically active amino acid sequence wherein the fusion protein self-assembles into particles containing a plurality of the same fusion protein and the particles exhibit biological activity of the second amino acid sequence.

2. A fusion protein comprising a first and second amino acid sequence wherein the first amino acid sequence is encoded for a yeast TYA gene sequence and the second amino acid sequence is encoded for by a gene sequence encoding a bacterial, viral, or protozoal antigen and wherein the fusion protein self-assembles into particles containing a plurality of the same fusion protein and the particles are antigenic.

3. A fusion protein comprising a first and second amino acid sequence wherein the first amino acid sequence is encoded for by a yeast TYA gene sequence and the second amino acid sequence is encoded for by a gene sequence encoding a therapeutically active amino acid sequence and wherein the fusion protein self-assembles into particles containing a plurality of the same fusion protein and the particles have therapeutic activity associated with the second amino acid sequence.

4. A fusion protein comprising a first and second amino acid sequence wherein the first amino acid sequence is encoded for by a yeast TYA gene sequence and the second amino acid sequence is encoded for by a gene sequence encoding a cytokine and wherein the fusion protein self-assembles into particles containing a plurality of the same fusion protein and the particles have cytokine activity.

5. A fusion protein according to claim 2 comprising a first and second amino acid sequence wherein the first amino acid sequence is encoded for by a yeast TYA gene sequence and the second amino acid sequence is encoded for by a gene sequence which encodes a viral antigen and wherein the fusion protein self-assembles into particles containing a plurality of the same fusion protein and the particles have antigenicity of the viral antigen.

* * * * *